United States Patent [19]
Portetellie et al.

[11] Patent Number: 5,239,056
[45] Date of Patent: Aug. 24, 1993

[54] PEPTIDE FRACTIONS WHICH INDUCE ANTIBODIES PROTECTING AGAINST THE BOVINE LEUKEMIA VIRUS, A PROCESS FOR OBTAINING SUCH FRACTIONS, THEIR CODING SEQUENCES AND VACCINES MADE FROM SUCH FRACTIONS

[75] Inventors: Daniel G. J. G. Portetellie, Meux-la Bruyere; Arséne Léon G. Burny, Gembloux; Corine F. Dandoy, Braine le Comte; Hélène S. C. Gras, nec Masse, Pont a Marq; André L. Tartar, Vitry en Artois, all of France

[73] Assignee: Rhone Merieux, France

[21] Appl. No.: 830,450

[22] Filed: Feb. 5, 1992

Related U.S. Application Data

[63] Continuation of Ser. No. 171,337, Mar. 21, 1988, abandoned.

[30] Foreign Application Priority Data

Mar. 20, 1987 [FR] France ................. 87 03881

[51] Int. Cl.$^5$ ............ C07K 7/08; C07K 7/10; C07K 7/64; C07K 15/04
[52] U.S. Cl. ................... 530/317; 530/324; 530/326; 530/327; 530/806; 435/69.3; 435/69.7
[58] Field of Search ........... 530/350, 806, 324, 326, 530/387.1, 387.9, 327, 317; 435/69.3, 69.7

[56] References Cited

U.S. PATENT DOCUMENTS 4,663,436  5/1987  Elder et al. ............ 530/324
4,740,461  4/1988  Kaufmann ............ 435/69.1

OTHER PUBLICATIONS

Bruck et al. 1984, *Virology* 136:20–31.
Burny et al., 1985 Onderstepoort J. Vet. Res. 52: 133–144.
Bruck et al. 1983 Haematology and Blood Transf Jusion 28: 222–226.
Portetelle et al., *In Animals Effected by Bovine Leukemia Virus Antibodies to Envelope Glycoprotein GP51 are Directed Against the Carbohydrate Moiety*, Virology 105 (1): 223–233, 1980.
Poprtetelle et al., 1984 Comm. Eur. Communities, EUR 8471, Agriculture pp. 45–51.
Lerner, R. A. 1982 Nature 299: 592–596.
Geysen et al. 1991, "Multipin Peptide Synthesis-H Review", Mimeotoper, Coselco Minotopes Pty Ltd. pp. 1–12.
Bruck et al. 1982, *Virology* 122:353–362.
Schultz et al. 1984, *Virology* 135:417–427.
Sagata et al. 1985, *Virology* 82:677–681.
Rice et al., 1985 *Virology* 142:357–377.
Chemical Abstracts No. 103:52361h (1985) of Bruck et al. 1984 *Comm. Eur. Communities*, [Rep.] Eur 8471, Agriculture, 29–38 (Eng.).
J. Miller and M. Van Der Maaten (in Ann. Recherche Vet., pp. 871 to 877, 9 (1978)).
L. V. Patrascu et al. (in Rev. Med.-Virologie, p. 955 to 1002, 31 (1980)).
M. Mammerickx, D. Portetelle, A. Burney and J. Leunen (in Zlb. Vet. Med. B27, pp. 291 to 303 (1981)).
M. Onuna et al. (in Am. J. Vet. Res. 45, pp. 1212 to 1215 (1984)).
Parfanovich et al. (in Br. Vet. J. 139, pp. 137 to 146 (1983)).
D. Portetelle et al. (in an abstract appearing in J. Cell. Biochem. Subl. 10A (1986), p. 209).
G. H. Theilen et al. (in Current Tops in Veterinary Medicine and Animal Sciences 15, pp. 547 to 559 (1982)).
Bruck et al., Virology 122, 1982, pp. 342–352.

Primary Examiner—Robert A. Wax
Assistant Examiner—Keith C. Furman

[57] ABSTRACT

A peptide fraction inducing the formation of antibodies which protect against the bovine leukemia virus (BLV), wherein it includes a peptide sequence which reproduces all or part of the sequence of the glycoprotein envelope gp51 fragment of the BLV virus which bears at least one of the epitopes (F, G, H) responsible for the biological activity of the virus. This fraction may be the fragment itself or a synthetic peptide. Application is made to the preparation or search for antibodies, to diagnosis and to the preparation of vaccines.

10 Claims, 5 Drawing Sheets

```
           10        20        30        40        50        60        70        80        90       100
T15-2 HRCSLSLGNQQWHETYNQEAKFSISIDGILEAHNQSPFFRPRYTLFVNGYPKQYPPSGRRRFEARAHVTYDCEPRCPYVGADNFDCPHHHNASQA
LB285 ------------T-------A-----------PR------F--------------------------------------H---------
VdH   -----------A-------S-----------HK------S--------K---------------------------R---
PLK   ------------A-------S-----------[AK]------S------Q------------------------[R]

110       120       130       140       150       160       170       180       190       200
DQGSFYVNHQILFLHLHQCHGIFTLTHEIHGYDPLITFSLHK PDPPQPDFPQLNSDVPSYRSHALLLHQTARAFPDCAICHEPSPPHAPEIL YHKTI 210       220       230       240       250       260       270
SGSGRLALPDAQIFHVNTSLFNTTQGHHHPSQRLLFNYSOGNALLLPPISLVNI TVSSAPPTRVRR
-N--------------T-L--------------------------A---------
-S--------------T-S--------------------------A---------
-S--------------S-S--------------------------A---------
```

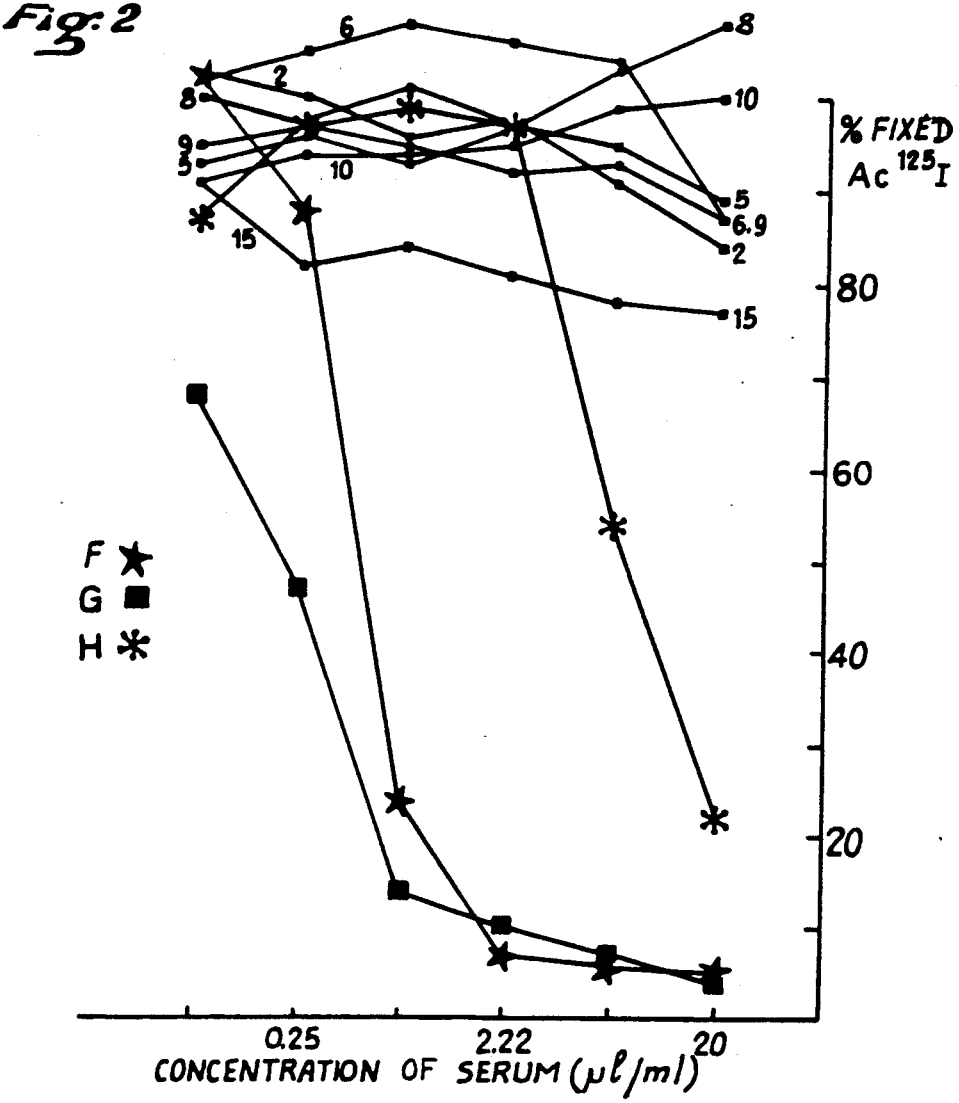
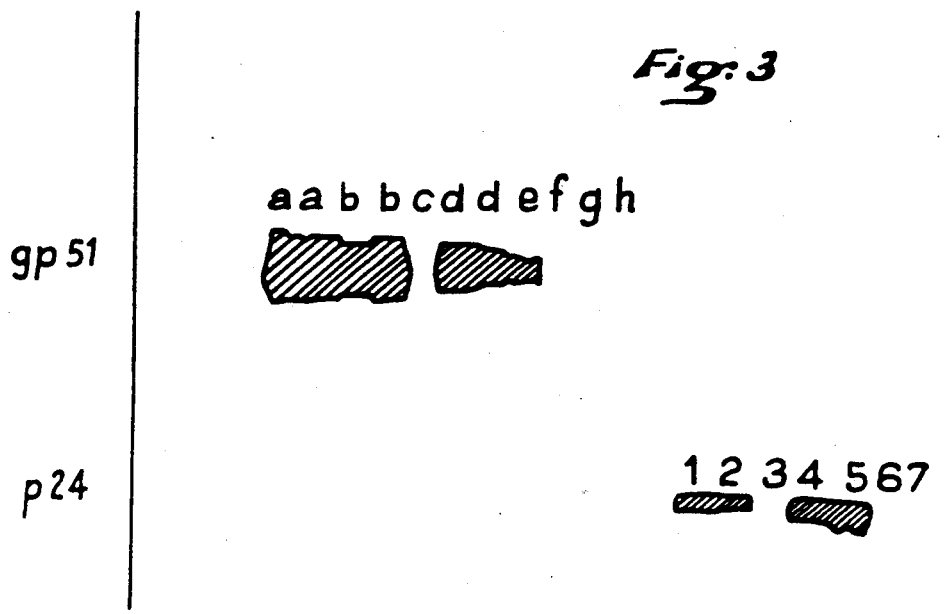

Fig. 5
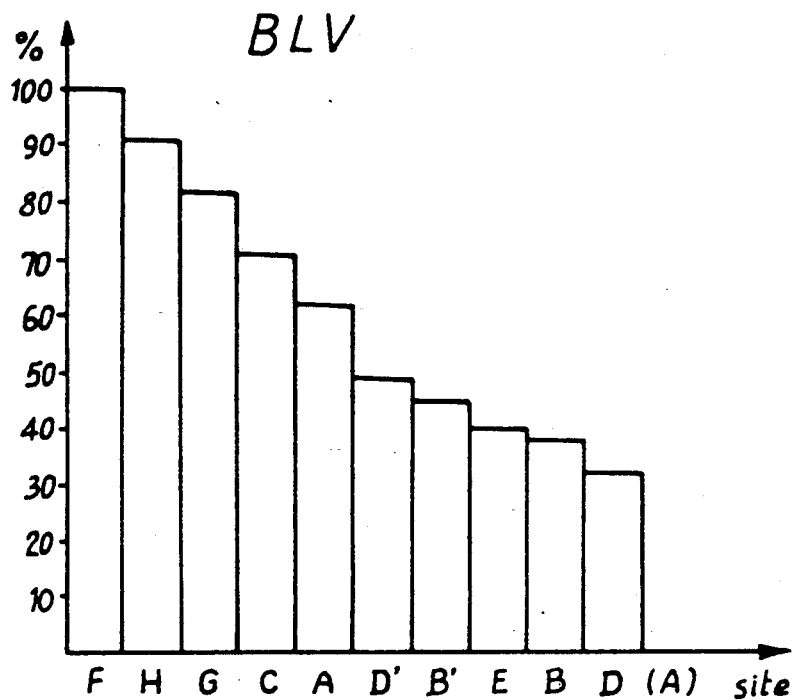
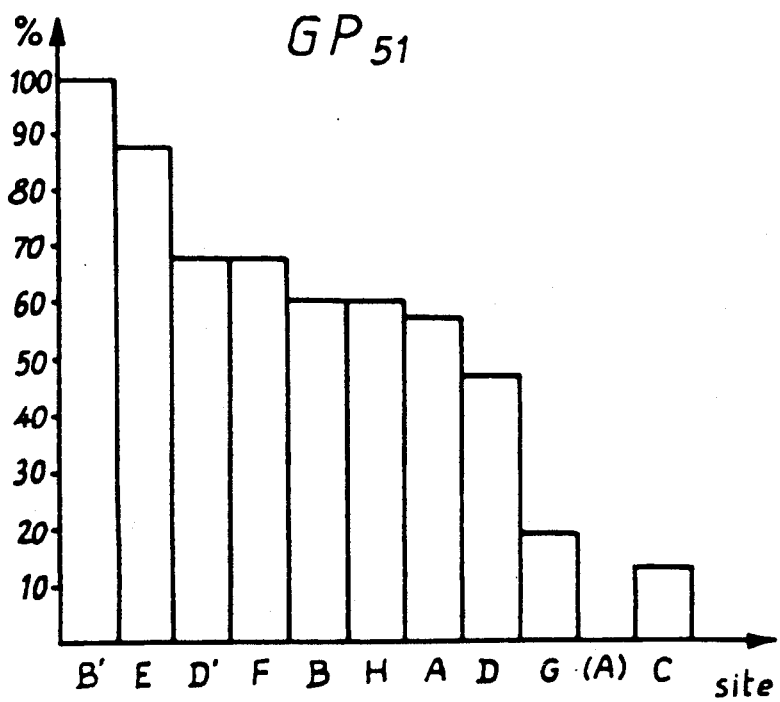

Fig. 6

PEPTIDE FRACTIONS WHICH INDUCE ANTIBODIES PROTECTING AGAINST THE BOVINE LEUKEMIA VIRUS, A PROCESS FOR OBTAINING SUCH FRACTIONS, THEIR CODING SEQUENCES AND VACCINES MADE FROM SUCH FRACTIONS

This application is a continuation of application Ser. No. 171,337 filed Mar. 21, 1988 now abandoned.

The present invention concerns new peptide fractions which induce protective antibodies against the bovine leukemia virus (BLV) as well as a process for obtaining such fractions.

It equally concerns vaccines made from these peptide fractions or from synthesized peptides which have in common with the said fractions, at least one antigenic site responsible for the biological activity of the virus.

Bovine leukemia, or enzootic bovine leukosis, is a highly contagious disease induced by a retrovirus, the bovine leukemia virus (BLV). This disease which strikes principally in Eastern Europe and in North and South America, attacks cattle, essentially the ovines and the bovines, leading to a quasi-generalized infection of the herds. This disease evolves relatively slowly, but in numerous cases, induces tumors, leading to the death of the infected animal. The development of this disease is all the more worrisome in that, at the present time, there is practically no means of combatting it or of avoiding its propagation. The solution up till now has been to isolate the infected animals and have them slaughtered.

For a number of years, the perfecting of a vaccine able to offer some protection against bovine leukemia has been sought.

J. MILLER and M. VAN DER MAATEN (in Ann. Récherche Vét., p. 871 to 877, 9 (1978)) mentioned the possibility of using glycoproteins from the envelope of the inactivated BLV virus as the active principle of a vaccine.

L. V. PATRASCU et al (in Rev. Méd.—Virologie, p. 955 to 1002, 31 (1980)) described the preparation of a vaccine called BL-VACC-RO, against the virus of bovine leukemia, obtained from an inactivated BLV virus.

M. MAMMERICKX, D. PORTETELLE, A. BURNY and J. LEUNEN (in Zbl. Vet. Med. B27, p. 291 to 303, (1981)) reported the results of studies which show that the passive antibodies acquired from the colostrum protect the animals from an infection.

M. ONUNA et al (in Am. J. Vet. Res. 45, p. 1212 to 1215 (1984)) noted that antibodies against the 51,000 molecular weight envelope glycoprotein of the BLV virus which is designated by the abbreviation gp51, shows a neutralizing activity against the BLV virus. This article set forth the vaccines made using the gp51 glycoprotein, the p24 protein and infected fetal lamb kidney (FLK) cells and which offer a certain protection when administered to sheep.

PARFANOVICH et al (in Br. Vet. J. 139, p. 137 to 146 (1983)) described the preparation of an inactivated BLV virus using aminomethylated compounds resulting from the reaction between formaldehyde and an amino acid such as leucine or lysine.

G. H. THEILEN et al (in Current Topics in Veterinary Medicine and Animal Sciences 15, p. 547 to 559 (1982)) indicated having vaccinated bovines with live cells from a BL-3 cell line obtained from the bone marrow and thymus of a sporadic case of bovine leukosis.

However, none of these vaccines conferred more than a very short-term protection nor were applied on a large scale.

It is known that, under certain conditions, the gp51 glycoprotein induces neutralizing antibodies.

C. BRUCK et al (in Virology 122, p. 342 to 352 (1982)) demonstrated 8 independent antigenic regions on the gp51 glycoprotein by anti-BLV monoclonal antibody competition.

D. PORTETELLE et al (in Comm. Eur. Communities (REP) EUR (1984), EUR 8471, Agriculture, p. 45 to 51) specified that three of these epitopes, F, G, and H, located on an apparently non-glycosylated fragment with a molecular weight of around 15,000 and obtained by digestion of the gp51 glycoprotein by a urokinase solution, are implicated in the neutralization of the virus. They foresaw the possibility of preparing an anti-BLV vaccine by insertion of the gene of the envelope gp51 or of a region corresponding to a biologically active site into a system of expression making glycosylation possible. They also envisaged the theoretical possibility of reproducing effective epitopes in the form of synthesized peptides.

D. PORTETELLE et al, in an abstract appearing in J. Cell. Biochem. Subl. 10A (1986), p. 209, suggested that the three epitopes, F, G, and H, could play an important role in the design of an anti-BLV sub-unit vaccine. These three epitopes are sensitive to the presence of a reducing agent, are localized on a weakly glycosylated fragment on the $NH_2$ terminal part of the glycoprotein, and are the only epitopes recognized on the undegraded virion. No lecture corresponding to that note was ever given.

One of the aims of the present invention is, based on these latter efforts, to develop peptide fractions susceptible of being incorporated into an effective vaccine.

Another aim of the present invention is to propose a fragment of gp51 which, in particular, induces the the formation of neutralizing antibodies, the said fragment being able to be used as the active principle of a vaccine against bovine leukemia.

Yet another aim of the invention is to provide synthesized peptides which, possibly coupled to a protein carrier or other appropriate carrier, are likely to induce antibodies which neutralize the biological activity of the BLV virus.

Still another aim of the invention is to provide synthesized peptides able to serve as reagents for detecting the presence of the BLV virus.

Still another aim of the invention is to provide a vaccine against bovine leukemia made either from the aforementioned gp51 glycoprotein fragment or from synthesized peptides, possibly coupled to a carrier.

Conforming to the invention, the antigenic sites or epitopes of the gp51 glycoprotein are demonstrated by monoclonal antibodies directed against the gp51 molecule.

These monoclonal antibodies are obtained by "the technique for the making of hybridomas" well-known in itself, consisting of the fusing of myelomatous cells and spleen cells from mice which have previously been immunized with the gp51 glycoprotein, then from the hybridomas formed, selecting those which secrete the monoclonal antibodies which are active against the gp51 glycoprotein.

The monoclonal antibodies permit the demonstration, notably by immuno-enzymzatic techniques, (for example, the ELISA method) or radio-immunologic techniques, of eight epitopes on the gp51 molecule which are designated A to H.

In order to locate the antigenic sites on the gp51 molecule which induce the formation of neutralizing antibodies, the gp51 glycoprotein was subjected to a controlled proteolytic digestion, for example with urokinase, which causes two fragments to be obtained; the first (fragment 1) has a molecular weight of around 35,000 and the second (fragment II) constituted of the weakly glysosylated NH$_2$ terminal part (the first 160 amino acids) has a molecular weight of around 15,000.

An immuno-precipitation of the peptide fragments with the monoclonal antibodies directed against each of the epitopes A to H, followed by an electrophoretic analysis on polyacrylamide gel, shows that the three epitopes F, G and H which induce the formation of neutralizing antibodies, are situated on fragment II while the epitopes A to D are to be found on fragment I having a molecular weight of around 35,000.

The peptide fraction which induces the formation of antibodies which protect against the bovine leukemia virus (BLV) conforming to the invention is characterized in that it includes a peptide sequence which reproduces all or part of the sequence of the fragment of glycoprotein envelope gp51 of the BLV virus which bears at least one of the epitopes responsible for the virus-neutralizing activity.

According to one of the embodiments of the invention, the peptide fraction is constituted of the gp51 fragment itself, this fragment being characterized in that:

it represents the NH$_2$ terminal part of the gp51 glycoprotein;

it presents a molecular weight of the order of 15,000 and is weakly glysosylated;

it bears, in an accessible position, the epitopes which induce the formation of neutralizing antibodies. These epitopes are themselves characterized in that:

they are recognized by the monoclonal antibodies directed against them;

they are selectively recognized by infected ovine and bovine serums;

they are sensitive to denaturation of the fragment by a reducing agent.

The neutralizing activity of the antibodies induced by the epitopes F, G and H has been determined by the pseudotype inhibition test described by J. ZAVADA, L. CERNY, A. ZADADOVA, J. BOZONOVA and A. D. ALSTEIN in J. Natl. Cancer Inst. 62, p. 95 to 101 (1979).

The peptide fraction conforming to the invention is obtained by subjecting the gp51 glycoprotein to a controlled proteolytic digestion, for example with a urokinase solution.

The peptide fragments obtained are immuno-precipitated by monoclonal antibodies. The protein-antibody complexes formed are then separated by electrophoresis on polyacrylamide gel in a sodium dodecylsulfate medium, then dissociated to obtain the desired fraction.

Starting from these results, the inventors have proceeded to the selection of the peptides intended for chemical synthesis, using procedures based on the prediction of the hydrophilic character of the peptide sequences, like, for example, the process described by KYTE and DOOLITTLE in the Journal of Molecular Biology 157, p. 105 to 123 (1982) or using procedures based on the prediction of the flexibility of the peptide chains, like, for example, the process described by KARPLUS and SCHULZ in Naturwissenschaften 72, p. 212 to 215 (1982).

The preferred peptides are constituted of, or include the following formula:

Glu-Pro-Arg-Cys-Pro-Tyr-Val-Gly-Ala-Asp-His-Phe-Asp-Cys-Pro this formula corresponding to the 78-92 sequence of the gp51.

The polypeptide may be linear or cyclic, cyclization occurring by S—S linking between the two cysteines.

Other interesting peptides may include the following sequences or be entirely constituted of them:

Pro-Asp-Pro-Pro-Gln-Pro-Asp-Phe-Pro-Gln-Leu-Asn;

Pro-Asp-Pro-Pro-Gln-Pro-Asp-Phe-Pro-Gln-Leu-Asn-Ser-Asp;

Cys-Pro-Arg-Ser-Pro-Arg-Tyr-Thr-Asp-Leu;

Cys-Ala-Lys-Ser-Pro-Arg-Tyr-Thr-Leu-Asp;

these formulas corresponding directly to sequences 144-155, 144-157 and 39-48 of the gp51 glycoprotein.

It goes without saying that there may be modifications to the free reactive groups which may be found on the various amino acid residues entering into the constitution of the peptide according to the invention, as long as such modifications do not incur a change in the immunogenic properties of the peptide as a whole. Peptides so modified naturally come within the scope of the present invention. Thus the —SH groups on the cysteine residue may be in the free thiol state, disulfide, (for example in the case of cyclic or dimerized peptides) protected by a protective group such as acetamidomethyl. Likewise the carboxyl groups may be acylated or esterified and the amine groups may be alkylated.

The peptides according to the invention may be prepared by classic techniques within the domain of peptide synthesis. This synthesis may be carried out in homogeneous solution or in solid phase.

For example, the technique of synthesis in homogeneous solution described by HOUDENWEYL in the book entitled "Methoden der Organischen Chemie" (Methods in Organic Chemistry) edited by E. Wünsch, Vol. 15-I and II, THIEME, Stuttgart 1974.

This method of synthesis consists of successively condensing, two by two, the successive aminoacyls in the required order, or condensing the aminoacyls and the previously formed fragments which already contain a number of aminoacyl residues in the appropriate order, or again several such previously prepared fragments, it being understood that care should be taken to first protect the reactive groups on these aminoacyls or fragments except for the amine groups of the one and the carboxyl groups of the other or vice versa, which need normally to intervene in the formation of peptide bonds, notably after activation of the carboxyl group, according to the well-known methods of peptide synthesis. As a variation, coupling reactions may be performed using the classic coupling reagents of the carbodiimide type, such as, for example, 1-ethyl-3-(3-dimethylaminopropyl)-carbodiimide. When the aminoacyl used has a supplementary amine group (as in the case of lysine, for example), or another acid group (as in the case of glutamic acid, for example), these functional groups would be protected, for example, by carbobenzoxy or t-butyloxycarbonyl groups for the amine groups, or by t-butylester groups for the carboxyl groups. Any other reactive group would be similarly protected. For example, when one of the aminoacyls in question contains an S group (cysteine, for example), an acetamidomethyl or paramethoxybenzyl may be used.

In the case of progressive synthesis, amino acid by amino acid, the synthesis begins preferably with the condensation of the C-terminal amino acid with the amino acid corresponding to the next aminoacyl desired in the sequence and so on, one after another, up till the N-terminal amino acid. According to another preferred method according to the invention, that described by R. D. MERRIFIELD in the article entitled "Solid Phase Peptide Synthesis" (J. Am. Chem. Soc., 85, p 2149 to 2154 (1963)) may be used.

To construct a peptide chain according to MERRIFIELD's process, a highly porous polymer resin is used, onto which the first C-terminal amino acid of the chain is attached. This amino acid is attached by the intermediary of its carboxyl group, and its amine group is protected, for example, by the group t-butyloxycarbonyl.

Once the first C-terminal amino acid is attached to the resin, the protective group is removed from the amine by washing the resin with an acid.

In the case where the amine-protecting group is t-butyloxycarbonyl, it may be eliminated by treating the resin with trifluoroacetic acid.

The second amino acid is then coupled to the C-terminal aminoacyl residue via the de-protected amine of the first C-terminal amino acid secured in the chain. Preferably, the carboxyl group of the second amino acid is activated, for example, by dicyclohexylcarbodiimide, and the amine is protected, for example, with t-butyloxycarbonyl.

Thus the first part of the desired peptide chain is obtained, which includes two amino acids and has its terminal amine protected. As above, the amine is then de-protected and the process of attaching the third aminoacyl, under conditions analogous to those for attaching the second C-terminal amino acid, may begin.

Thus are attached, one after the other, the amino acids which will constitute the peptide chain, onto the each-time newly de-protected amine group of that portion of the peptide chain which has already been formed, and which is anchored onto the resin.

Once the whole of the desired peptide chain has been formed, the groups protecting the various amino acids which make up the peptide chain are eliminated and the peptide is detached from the resin, for example, using hydrofluoric acid.

One may equally synthesize, or prepare in some other manner, a DNA sequence coding for a peptide according to the invention and introduce it, in association with a usual promoter, into an expression vector such as bacteria, yeast or a cell line.

The invention equally has as its object the DNA coding sequences for that purpose and the purified genes which are made up of or include these sequences.

Each DNA sequence may be determined from the acid sequence of the peptide according to the invention by a routine transposition.

Finally, it is also possible to produce peptides or polypeptides according to the invention by selective cleavage of the gp51 glycoprotein or of its fragment II.

The invention equally concerns the hydrosoluble oligomers of the afore-mentioned monomeric peptides. Oligomerization may cause an increase in the immunogenicity of the peptides according to the invention. While such a quantitative indication may in no way be considered as limitative, it may nevertheless be suggested that these oligomers may contain from 2 to 10 monomer units.

Any polymerization technique currently practiced in the domain of peptides may be employed to accomplish oligomerization; this polymerization being continued until the oligomer or polymer contains the required number of monomeric reactive units for the acquisition of the desired immunogenicity.

A preferred method of oligomerization or monomer polymerization consists of reacting the monomer with a crosslinking agent such as glutaraldehyde.

Other methods of oligomerization or coupling may also be used, for example that of successive couplings of monomeric units by the intermediary of their carboxyl and amine terminal functional groups or other reactive groups, for example —SH, in the presence of homo- and heterobifunctional coupling agents.

The invention also concerns the conjugates obtained by covalent coupling of the peptides according to the invention or of the afore-said oligomers to porous molecules which may be natural proteins or the viral proteins themselves or again synthetic, physiologically acceptable and non-toxic carriers, by the intermediary of complementary reactive groups respectively to be found on the carrier molecule and on the peptide. Examples of appropriate groups are illustrated in what follows.

As examples of carrier molecules or macromolecular carriers entering into the constitution of the conjugates according to the invention, may be mentioned such natural proteins as the tetanus anatoxin, ovalbumin, the serum albumins, Keyhole Limpet hemocyanin, thyroglobulin, etc.

As examples of synthetic macromolecular carriers, may be mentioned, for example, the polylysines or the poly(D-L-alanine)-poly(L-lysine)s.

The literature mentions other types of macromolecular carriers susceptible of being used; in general these have a molecular weight above 20,000.

To synthesize the conjugates according to the invention, processes already known in themselves may be used, such as that described by FRANTZ and ROBERTSON in Infect. and Immunity, 33, p. 193 to 198 (1981), or that described by P. E. KAUFFMAN in Applied and Environmental Microbiology, October 1981, Vol. 42, No. 4 p. 611 to 6140 using the peptide and the appropriate carrier molecule.

In practice, the following compounds, cited in a non-limiting way, may be advantageously used as a coupling agent: glutaric aldehyde, ethyl chloroformiate, hydrosoluble carbodiimides [N-ethyl-N'(3-dimethylaminopropyl) carbodiimide, HCl], diisocyanates, bis-diazobenzidine, di-and trichloro-s-triazines, cyanogen bromides, and benzaquinone, as well as the coupling agents mentioned by AVRAMEAS, TERNYNCK and GUEDSON in Scand. J. Immunol., Vol.8, p. 7 to 23 (1978).

Any coupling process implicating, on the one hand, one or more reactive groups of the peptide, and, on the other hand, one or more reactive groups of the carrier molecules, may be used. Advantageously, these would be the carboxyl and amine groups, which are able to give rise to a coupling reaction in the presence of a coupling agent of the sort of those used in protein synthesis, for example, 1-ethyl-3-(3-dimethylaminopropyl)-carbodiimide, N-hydroxybenzotriazole, etc. Glutaraldehyde may also be used, notably when linking together amine groups respectively to be found on the peptide and on the carrier molecule.

It is equally possible to associate two or more synthetic peptides conforming to the invention by covalent or other association, between each other or onto any protein carrier.

The synthetic oligopeptides, once administered to the animal, induce in it antibodies capable of recognizing in the virus, the amino acid sequence corresponding to the synthetic constituents.

The peptides conforming to the invention may naturally be prepared by means other than chemical synthesis, for example by using bacteria transformed by vectors carrying a nucleotide sequence corresponding to the amino acids.

It is also understood that peptides in which certain amino acid sequences may be modified, without appreciably modifying the immunological properties of the peptide in question, equally come within the scope of this invention.

The present invention also has for object the vaccines obtained either from the fragment of the gp51 glycoprotein having a molecular weight of the order of 15,000, or from synthetic peptides which induce the formation of neutralizing antibodies, of the said gp51 fragment, and more particularly the peptide 78-92, coupled or not to a carrier.

The vaccinating compositions, which associate the peptide fraction or the synthetic peptides with pharmaceutical excipients and/or adjuvants, generally are presented in the form of injectable solutions. Preferably, unitary doses would be small and not exceed 1 µg/kg of live weight.

The adjuvants used are, either oily adjuvants and emulsified with the antigen, or of the absorbent type such as aluminum hydroxide.

Other characteristics and advantages of the invention will become apparent in the reading of the rest of the description which follows, and in referring to the attached drawings.

BRIEF DESCRIPTION OF THE DRAWINGS

FIG. 2 illustrates the results obtained in the fixation tests during which monoclonal antibodies specific to the eight gp51 epitopes were put in the presence of increasing quantities of infected bovine serum;

FIG. 3 illustrates the results of a Western Blot analysis of BLV viral particles;

FIG. 5 illustrates the reactivity of different monoclonal antibodies with various gp51 preparations;

FIG. 6 represents the amino acid sequences of the gp51 glycoprotein established from the DNA sequence of four BLV variants;

MONOCLONAL ANTIBODY PREPARATION

Immunizing the Mice

Figure 1:
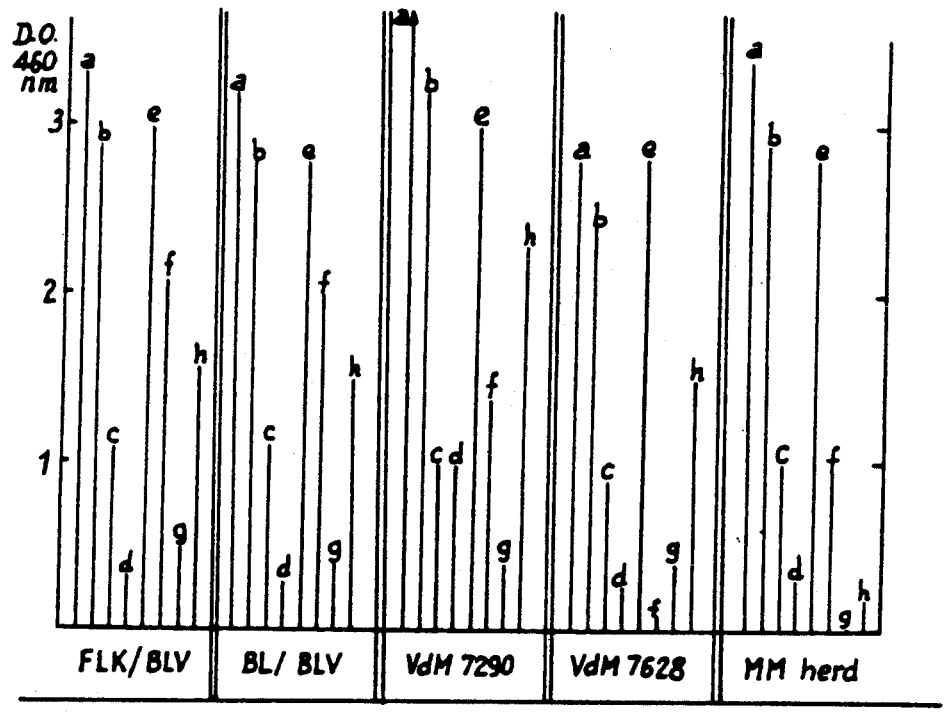
FIG. 1 illustrates the demonstration of the eight epitopes of the glycoprotein gp51 by the ELISA test, using monoclonal antibodies.

Balb/c mice were injected sub-cutaneously or intraperitoneally with 50 µg of gp51 in the presence of complete Freund's adjuvant. This injection was repeated 2 weeks later using incomplete Freund's adjuvant and again 4 weeks later with no adjuvant. Two months later, they were injected one last time intraperitoneally and intraveinously.

Cell Fusion

Hybrids were prepared by fusion of mouse myeloma cells with spleenocytes from immunized mice according to the technique described by L. A. HERZENBERG et al in "Handbook of Experimental Immunology" (D. WEIR, ed.) 25, p. 1 to 25 (Blackwell, London).

The hybrids obtained were distributed on plates containing 96 wells and selected using HAT medium in the presence of mouse macrophages and thymocytes. The hybrids producing anti-gp51 antibodies were detected using a radio-immuno-assay in liquid phase with the anti-gp51 antigen labelled with iodine 125, or using a radio-immuno-assay in solid phase with the BLV virus absorbed in the wells of the micro-plates. In this latter case, the specific antibodies absorbed on the virus were detected with mouse anti-immunoglobulin labelled with iodine 125. After washing, the radioactivity absorbed onto the specific complexes was revealed by autoradiography.

The productive clones selected were transferred onto plates of 24 wells and sub-cloned in a semi-solid agarose medium.

The hybrid cells obtained were injected into the intraperitoneal cavity of mice first treated with pristane. After 10 to 15 days, the ascites containing considerable quantities of the desired monoclonal antibodies, were collected.

These monoclonal antibodies were purified by ion-exchange chromatography on DEAE-AFFIGEL BLUE according to the method described by BRUCK et al in J. Immunological Methods 53, p. 313 to 319 (1982).

These monoclonal antibodies were labelled with iodine 125 by the chloramine T process described by F. C. GREENWOOD et al in Biochemical Journal, 89, p. 114 to 123 (1963).

The specificity of the different monoclonal antibodies obtained, for the given epitopes was determined by assaying the competition between the antibodies for the gp51 antigen absorbed in the wells of the microtitration plates.

To do this, one microgram of unlabelled purified monoclonal antibodies was incubated overnight at 4° C., in a volume of 50 µl in the wells of plastic microtitration plates containing the absorbed gp51 (50 ng).

Antibodies radioactively labelled with iodine 125 (10 ng–100,000 cpm) were then added and the incubation continued for a further 6 hours at 4° C.

The microplates were then intensively washed and the radioactivity attached to the plastic in each of the wells was measured in a counter.

The results were interpreted knowing that, if two antigenic sites are very close or identical, the linking of the first (unlabeled) antibody to its epitope, will perturb or prevent the linking of the second (labelled) antibody to its epitope.

Competition assays between the purified monoclonal antibodies have allowed eight independent antigenic sites on the gp51 molecule, designated by the letters A, B, C, D, E, F, G, and H, to be defined.

THE ELISA METHOD FOR DETECTING BLV VARIANTS

This method was applied according to the following conditions:

300 ng of purified monoclonal antibodies directed against a given antigenic site, were fixed to the walls of the wells of a microtitration plate;

after washing and saturation with an inert protein, bovine albumin, dilutions of the viral proteins obtained from the various BLV isolates (in the presence of the inert protein and the detergent TWEEN 80) were introduced and the plates incubated for 16 hours at 4° C.;

after washing, monoclonal antibodies directed against the antigenic sites, were attached to the gp51 antigen and coupled to the enzyme peroxidase, then incubated for 4 hours at 4° C.;

after washing, the enzymatic activity associated with the complexes was revealed with the aid of the substrate $H_2O_2$ plus O-phenylene diamine;

after 15 mn, the reaction was stopped with 6N HCl and the optical densities measured using a microtitration plate spectrophotometer.

FIG. 1 shows the results of an ELISA test carried out on BLV viral particles of diverse origins:

FLK/BLV: a BLV bovine leukemia virus cultivated on fetal lamb kidney cells;

BL/BLV: a BLV virus cultivated on bat lung cells;

Vd M 7290 and Vd M 7628: two BLV isolates provided by Dr. Martin Van der Maaten, Ames, Iowa (USA); and MM herd: a BLV isolate provided by Dr. Marc Mammerickx (Belgium).

The optical density (O.D.) at 490 nm appears along the ordinate and each vertical bar represents the reactivity of monoclonal antibodies directed against the epitopes A to H. It may be seen that the monoclonal antibodies directed against the epitopes A, B and E show greater reactivity with these epitopes, while that shown by the monoclonal antibodies directed against the epitopes F, G and H, is weaker. It may be observed that the epitopes F from the VdM 7628 isolate, and G from the MM herd isolate, are virtually non-existent as a result of mutations having occurred.

ANTIBODY ATTACHMENT TEST

This test was carried out according to the following conditions:

a determined quantity of gp51 antigen was fixed for each of the monoclonal antibodies by using different dilutions of the antigen; the dilution capable of binding 50% of the maximal radioactivity able to be fixed, was chosen; this attachment was carried out in the wells of a microtitration plate;

dilutions progressing by factors of three of the serum of bovine origin to be tested, were introduced into a series of wells (initial concentration: 1 µl of serum in a volume of 50 µl in the wells) and the microplate incubated for 5 hours at ambient temperature;

then 50 µl of a solution containing 10 ng of monoclonal antibodies radioactively labelled with iodine 125 were introduced and the plates incubated overnight at 4° C.;

the plates were then washed and the fixed radioactivity loosed with the help of a 2% solution of sodium dodecylsulfate (SDS);

the fixed radioactivity was measured in a gamma counter and expressed as a percentage of the radioactivity adsorbed in the presence of a non-competing normal bovine serum.

FIG. 2 shows the results obtained from the attachment (fixing) tests in which labelled monoclonal antibodies directed against the eight epitopes of gp51 are placed in competition with decreasing quantities of infected bovine serum (case of tumor No. 15). The abscissa shows the concentration of the serum (expressed in ul/ml) and the ordinate shows the quantity of labelled monoclonal antibodies which were fixed (expressed in %).

The curve using the asterisk (*) symbols is that obtained for the monoclonal antibodies specific to the epitope H.

The curve using the star symbols is that obtained for the monoclonal antibodies specific to the epitope F.

The curve using the solid square symbols is that obtained for the monoclonal antibodies specific to the epitope G.

The curves referenced 2—2, 5—5, 6—6, 8—8, 9—9, 10—10, and 15—15 are those obtained for the monoclonal antibodies directed respectively against the epitopes B, D, E, C, A, B', and D' of gp51.

As may be seen on this figure, only the monoclonal antibodies directed against the epitopes F, G and H are displaced by the bovine antiserum.

WESTERM BLOT TECHNIQUE

This technique was applied according to the following conditions:

suspension of the BLV virus obtained by ultrafiltration and ultracentrifugation;

denaturation of the complete virus by heating to 100° C. for 5 mn in the presence of SDS and a reducing agent, mercapto-ethanol;

separation of the viral proteins by electrophoresis on a 15% polyacrylamide gel, in the presence of SDS;

electric transfer of the proteins thus separated, onto a nitrocellulose membrane (electrophoresis buffer without SDS, 2 hours at 4° C. under an intensity of 0.5 A);

saturation of the membrane with an inert protein, serum albumin, and cutting the membrane into strips;

incubation of each strip with the monoclonal antibodies under study which are directed against the antigenic site of gp51, and against the p24 protein as a control (16 h at 20° C.);

after washing, incubation of the strips with a mouse antiimmunoglobulin rabbit serum (2 hours at 20° C.);

after washing, incubation of the strips with a preparation of protein A labelled with iodine 125 (1 h at 20° C.);

after washing and drying, autoradiography of the strips;

photographic development and observation of the marks corresponding to the viral proteins being sought.

FIG. 3 illustrates the results of the Western Blot analysis of the BLV viral particles. In the margin to the left of the figure are indicated the viral proteins. The channels indicated by the titers show the reactivity of the gp51 glycoprotein with the monoclonal antibodies specific to the epitopes A, A', B, B', D, D', E, F, G, and H. The absence of colored marks in the channels C, F, G and H show that the corresponding epitopes were denatured by the initial treatment of the sample. The channels tagged with numbers show the results for the various monoclonal antibodies directed against the p24 protein which is the major internal protein of the BLV virus.

In FIG. 5 is illustrated the reactivity of the different monoclonal antibodies with, on the one hand, whole BLV viral particles, and on the other hand, a purified gp51 glycoprotein. The conditions of the reactions were as follows:

attachment of the antigen onto the walls of each of the wells of a microtitration plate, using 400 ng of purified viral suspension per well, or 50 ng of purified gp51 antigen per well;

after washing and saturation with an inert protein (bovine serumalbumin), introduction into the wells of 200 μl of serial dilutions of the purified monoclonal antibodies to be tested (1:20, 1:60, 1:180, 1:540, 1:1620, 1:4860, 1:14580, 1:43740); incubation of the reaction for 16 h at 4° C.;

after washing, addition of 10 ng per well of mouse antiimmunoglobulin goat immunoglobulin Fab fragments, coupled to the enzyme peroxidase; incubation for 2 h at 4° C.;

after washing, revelation of the enzymatic activity associated with the walls with the aid of the substrate $H_2O_2$ plus O-phenylene diamine;

after 15 mn, the reaction was stopped with 6N HCl and the optical densities measured using a microtitration plate spectrophotometer.

For each antibody, the results are expressed as a percentage of the mean optical density at dilutions 1/20 and 1/60 of the monoclonal antibodies giving the maximal optical density in the test considered.

The antigenic sites recognized by the different monoclonal antibodies are shown along the abscissa.

It may be seen that the reactivity of monoclonal antibodies with the BLV viral particles is quite great. The epitopes F, G and H are probably the only epitopes recognized by the non-degraded viral particles. These monoclonal antibodies are, on the other hand, weakly reactive to the purified gp51, in particular site G.

PREPARATION OF THE gp51 FRAGMENT HAVING THE MOLECULAR WEIGHT OF THE ORDER OF 15,000

Radioactively labelled gp51 was subjected to a controlled enzymatic digestion using the protease urokinase.

The lyophilized enzyme was provided by the company ABBOTT LABORATORIES, Ivry-sur-Seine (France). This enzyme was resuspended to a final concentration of 2 mg/ml.

The purified gp51 antigen was radioactively labelled either with iodine 125 by the chloramine T method of F. C. GREENWOOD et al (Biochemical Journal (1963), 89, p. 114-123), or by tritiating the lysine residue of the molecule using the technique of methylation and sodium borohydride reduction described by B. F. TACK and R. L. WILDER in Methods in Enzymology 73, p. 138-147 (1981) and slightly modified by C. BRUCK et al in Virology 122, p.353-362 (1982).

To 1 ml of a solution containing 10 ng of $^{125}I$-gp51 or 11 ug of $^3H$-gp51, is added 50 μl of the urokinase preparation. After 45 mn of incubation at 37° C., again 50 μl of the same urokinase preparation is added, and again after 90 mn of incubation.

After a total incubation time of 135 mn, the urokinase activity is blocked by an inhibitor of the protease, phenylmethylsulfonylfluoride (PMSF) at a concentration of $10^{-4}M$.

The peptide fragments obtained were then immunoprecipitated with the aid of the monoclonal antibodies in the following manner.

Into a final volume of 200 μl of isotonic phosphate buffer at pH 7.2 containing 0.2% bovine serumalbumin and 0.2% Tween 80, is mixed 5 μl of ascitic liquid containing the monoclonal antibodies to be tested along with a 25 μl sample of the gp51 digested by the urokinase.

After 20 hours of incubation at 4° C., 100 μl of buffer containing 1 μl of rabbit serum directed against mouse immunoglobulins is added, and incubated again for 20 hours at 4° C.

The antigen-antibody complexes are immunoprecipitated with 50 μl of a 10% preparation of *Staphylococcus aureus-protein* A for 30 mn at 4° C.

The *Staphylococcus aureus*-protein A preparation is collected by centrifugation and washed several times with phosphate buffer at pH 4 containing 0.5% Triton X-100 and 0.5% deoxycholate.

The suspension of *Staphylococcus aureus*-protein A in 100 μl of electrophoresis buffer is then heated to 100° C. for 3 mn and centrifuged to eliminate the bacteria.

The supernatant containing the dissociated antigen-antibody complexes is collected and the proteins are separated by electrophoresis on 2% polyacrylamide-SDS gel.

After electrophoresis, the gel is fixed, dried and subjected to autoradiography.

After autoradiography, the results show that the monoclonal antibodies directed against the antigenic sites A, B, C and D recognize a fragment of around 35,000 daltons (fragment I).

On the other hand, the monocional antibodies directed against the antigenic sites (E), F, G and H recognize a fragment of around 15,000 daltons (fragment II).

LOCALIZATION OF THE F, G AND H EPITOPES ON THE FRAGMENT HAVING A MOLECULAR WEIGHT OF THE ORDER OF 15,000

Figure 6:
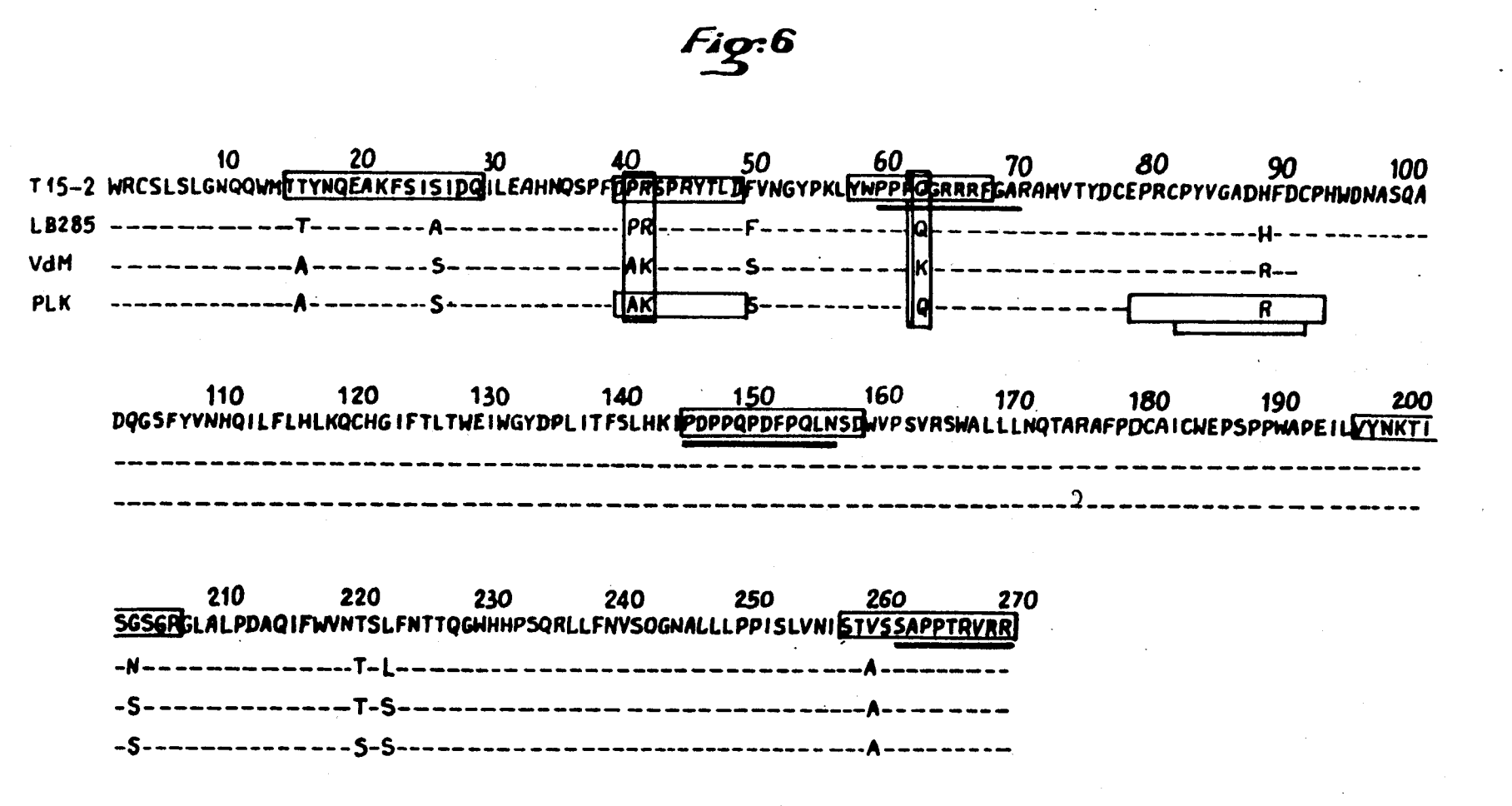

The complete sequence of the gp51 antigen was easily able to be deduced from the nucleotide sequence of the envelope gene which codes for this glycoprotein (FIG. 6).

Figure 4:
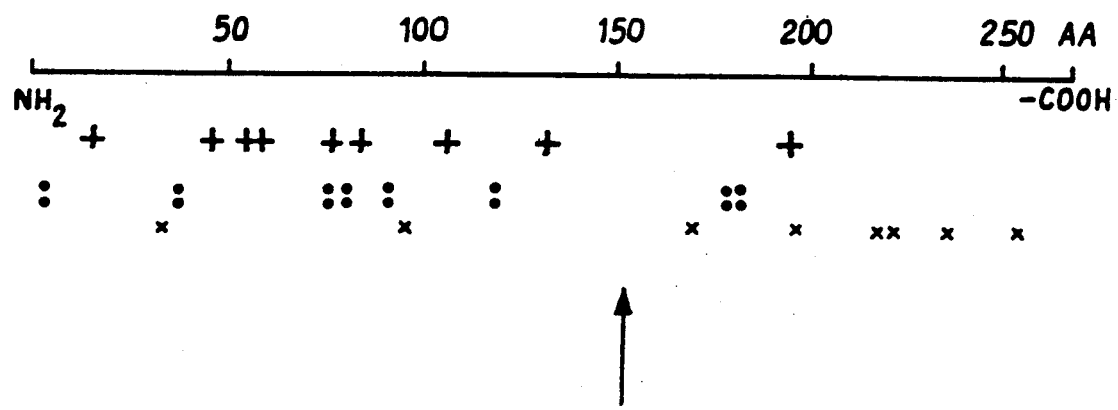
FIG. 4 schematically represents the gp51 molecule and the point at which the cleavage occurs.

In FIG. 4, the gp51 molecule is represented schematically along with the possible glycosylation sites and the point (shown by the arrow) at which the cleavage of the molecule occurs.

The symbols employed have the following signification:

+ represents tyrosine
: represent cysteine
× represents a potential glycosylation site.

Cysteine plays an important role because it permits, by its thiol groups, the cyclization of the peptide and the spatial structure of the epitopes F, G and H. Tyrosine, by its hydroxyl group, permits the labelling of the peptide with a radioisotope, iodine 125.

The experimental results show that:

a) The sites E, F, G and H, defined by the monocional antibodies, occur on fragment II, which is very little glycosylated. In addition, analysis of the amino acid sequence of gp51 reveals that its $NH_2$ part has few possible glycosylation sites (only 2 instead of the 6 which the COOH terminal part has).

b) After controlled digestion of the gp51 antigen labelled with iodine 125 at its tyrosine units (by the chloramine T method), using a highly diluted preparation of proteinase K, the monoclonal antibodies directed against the sites E, F, G and H precipitate more than 90% of the radioactivity used, while, under identical conditions, the monoclonal antibodies directed against the sites A, B, C and D don't even precipitate 11% of the radioactivity. These results show that the epitopes E, F, G and H are to be found in a region very rich in tyrosine which fixes iodine 125, which is the case for the $NH_2$ terminal part of gp51 (which has 8 tyrosines while the COOH terminal part has only one).

c) The Western Blot experiment (FIG. 3) carried out in the presence of SDS (dodecylsulfate) detergent and reducing agent (mercaptoethanol) demonstrates the denaturation of the antigenic sites (C), F, G and H by the absence of reactivity with the monoclonal antibodies. In addition, radioimmunologic measurement of the gp51 antigen labelled with iodine 125, demonstrates the absence of reactivity with the monoclonal antibodies directed against the sites (C), F, G and H, if the antigen was first treated with 10 mM of the mercaptoethanol reducing agent for 15 mn.

These results make it apparent that the denaturation of the C, F, G and H sites is due, above all, to the presence of the reducing agent. It must then be deduced that these antigenic sites possess an antigenic structure dependent upon the disulfide bonds. It should be noted that the $NH_2$ terminal end is very rich in cysteine (6 residues while the COOH terminal end has only 2).

The results set forth under a) b) c) show that fragment II bearing the E, F, G and H epitopes, is the $NH_2$ terminal part of the gp51 antigen.

The biological activities associated with antipeptides confirm these results.

OLIGOPEPTIDE PREPARATION

The synthesis of the peptides figuring in Table 1 was undertaken using the solid phase process described by MERRIFIELD in J. Am. Chem. Soc. (1963), 45, p. 2149–2154.

In this table, the letters L and B indicate that the peptides are of different origins. In the column indicating the amino acid sequences, the slight variations which may occur within the sequence of the same peptide have been underlined (as in the case for peptide L 39-48). In this same table, we have also indicated the cyclized variant of the peptide L 78-92. The amino acid sequences of the glycoprotein gp51 are represented in FIG. 6, these have been established from the DNA sequence of 4 variants of the BLV virus (T15-2: tumor case No. 15; LB 285 and VdM: two viral isolates; and FLK: BLV virus cultured on fetal lamb kidney cells).

The letters representing the amino acids have the following meanings: A-Ala, C-Cys, D-Asp, E-Glu, F-Phe, G-Gly, H-His, I-Ile, K-Lys, L-Leu, M-Met, N-Asn, P-Pro, Q-Gln, R-Arg, S-Ser, T-Thr, V-Val, W-Trp, Y-Tyr.

The amino acid sequences appearing in boxes, as well as those which are underlined, are those peptides which have been chemically synthesized.

OLIGOPEPTIDE SYNTHESIS

The synthesis was carried out using MERRIFIELD's solid phase technique. The peptide chain is prepared starting from a first C-terminal amino acid covalently attached to a polymer of styrene and divinylbenzene (which could equally be of a polyamide type) by a bond of the benzylic ester type (chloromethylated resin) or of the amide type (benzhydrylamine resin). The amino acids following on toward the N-terminal end, are added successively by the repetition of cycle of operations, the principle steps of which are:

1) de-protection of the Boc group (tertiobutyloxycarbonyl, used to protect the amine functions) by using trifluoroacetic acid (TFA) in solution in $CH_2Cl_2$;

2) neutralization of the aminated functions by using diisopropylamine (DIEA) dissolved in $CH_2Cl_2$;

3) coupling carried out by activation of the carboxylic functions of the amino acids to be introduced by using dicyclohexyl-carbodiimide or by the preparation of activated esters (of orthonitrophenol, for example). The different coupling reagents are added in excess (3 to 6 times) relative to the resin.

After the coupling operation, the absence of free amine groups on the resin is verified by the ninhydrine test. In the case of a positive reaction, the coupling is repeated.

During the synthesis, the reactive groups on the side chains of the amino acids are protected by the use of the groups figuring in Table II.

At the end of the synthesis, the peptide is freed from the resin and from its protective groups by a one-hour treatment with anhydrous hydrofluoric acid containing 10% p-cresol (V/V) and 5% dimethylsulfide (V/V).

Only the acetamidomethyl (acm) groups protecting the cysteines remain intact after this treatment.

The peptide is then purified by gel filtration and reverse phase partition chromatography.

Its identity is checked by analysis of the amino acids after acid hydrolysis and its homogeneity by chromatography on a silica layer in three different solvent systems, as well as by reverse phase high pressure liquid chromatography (RP-HPLC).

DE-PROTECTION AND CYCLIZATION OF PEPTIDE 78-92

20 mg (11.6 μmoles) of peptide 78-92, its two cysteine residues protected by S-acetamidomethyl groups, are dissolved in 1 ml of a de-gassed aqueous solution of acetic acid at pH 4.

8 mg (25 μmoles) of mercuric acetate are added. The reaction is allowed to continue at ambiant temperature for 3 hours under a nitrogen atmosphere and while being stirred. The reaction medium is then diluted with 15 ml of de-gassed water then is bubbled with $H_2S$ for 10 mn while being stirred. The solution is filtered on No. 4 fritted glass, then de-gassed by nitrogen bubbling for 2 hours. Again it is diluted, with 200 ml de-gassed water, and the pH adjusted to 7.5 using diluted ammonia. Reoxidation is accomplished by bubbling with air for 20 hours. The reaction medium is then lyophilized. The cyclic peptide obtained is purified by filtration on ultra-fine Biogel P2. The homogeneity is monitored on TLC in different solvent systems and by RP-HPLC relative to a non-protected control.

Its identity is checked by analysis of the amino acids after total acid hydrolysis and by measuring its molecular weight by F.A.B.S. (Fast Atom Bombardment Spectroscopy).

Starting with the peptide thus obtained, an oligomer having reinforced immunogenic properties may be obtained by proceeding as follows:

5 mg of the afore-said peptide dissolved in a 0.1M solution of sodium bicarbonate are mixed with an aqueous solution of 25 g of glutaraldehyde per liter to obtain a final peptide concentration of 0.1%. The reaction takes place at ambiant temperature, in the dark and while being stirred, for 5 days. The oligomer formed may then be dialyzed against an appropriate buffer such as PBS.

COUPLING THE OLIGOPEPTIDES TO THE CARRIER

To couple the peptides according to the invention to an appropriate carrier molecule such as Keyhole limpet hemocyanine or thyroglobulin, in order to reinforce its immunogenicity, one of the following methods may be used in the presence of homo-bifunctional or hetero-bifunctional agents also described below.

I—Homo-bifunctional agent, such as glutaraldehyde; the experimental conditions may be summarized as follows:

2.5 mg of a macromolecule (protein or synthetic) dissolved in 2.5 ml of 0.1M sodium bicarbonate is mixed with 21 mg of peptide. After one hour of contact under stirring and at ambiant temperature, glutaraldehyde is added in two steps so as to obtain a final concentration of 0.1% of the coupling agent. The contact is maintained at ambiant temperature and in the dark for 5 days. The conjugate formed is then collected after dialysis of the solution against PBS.

II—Hetero-bifunctional agent, linking the following functional groups:

1. amine and carboxyl:
method of mixed anhydrides:
The experimental conditions followed correspond to the general process described by M. L. TILAK in Tetrahedron Letters 11, p. 849–854 (1979).

2. carboxyl and amine or alcohol:
method using a hydrosoluble carbodiimide:
The experimental procedure is that described by T. L. GOODFRIEND et al in Science 144, p. 1344 (1964).

3. amine and sulfhydryl:
numerous agents are used, however the most common are:

a) 6-maleimido-caproic-acyl-N-hydroxy-succinimide-ester (MCS). The coupling procedures using this reagent are described by LEE et al in Molec. Immunol. 17, p. 749–756 (1980).

b) N-succinimidyl-3(s-pyrridyl-dithio) propionate (SPDP). The method employed was described by CARLSON et al in Biochem J. 173, p. 723–727 (1978).

IMMUNIZATION OF THE ANIMALS

Rabbits aged around three months were injected intradermally three times at 15-day intervals using preparations of conjugates made up of 1 ml of isotonic phosphate buffer containing 500 μg of carrier molecules, Keyhole limpet hemocyanine, emulsified with an equal volume of complete Freund's adjuvant. The blood was drawn 8 days after the third injection and the serum collected to carry out various evaluations.

DETECTION OF ANTIBODIES

Antibodies were detected using the ELISA method according to the following conditions:

attachment of the antigen onto the walls of each of the wells of a microtitration plate, using 400 ng of purified viral suspension per well, or 50 ng of purified gp51 antigen per well, or 50 ng of synthetic peptides per well;

after incubation, washing and saturation with an inert protein (bovine serumalbumin), introduction into the wells of 200 μl of serial dilutions of the antiserum to be tested (dil. 20, 60, 180, 540, 1620, 4860, 14580, 43740); incubation of the reaction for 16 h at 4° C.;

after washing, addition of 100 μg per well of buffer containing 10 ng of protein A coupled to the enzyme peroxidase if the antiserums come from rabbit, or addition of 100 μg per well of buffer containing 100 ng of antibodies purified by affinity chromatography and directed specifically against the immunoglobulins of the antiserums used in the dilutions, and coupled to the enzyme peroxidase; incubation for 2 h at 4° C.;

after washing, revelation of the enzymatic activity associated with the walls with the aid of the substrate $H_2O_2$ plus O-phenylenediamine;

after 15 mn, the reaction was stopped with 6N HCl and the optical densities measured using a microtitration plate spectrophotometer.

The ELISA test was used to study the reactivity of the antipeptide serums against the synthetic peptides themselves and against the natural peptides. The results obtained are presented in Table III.

As a control, a rabbit antiserum against the purified gp51 antigen was tested.

Figure 7:
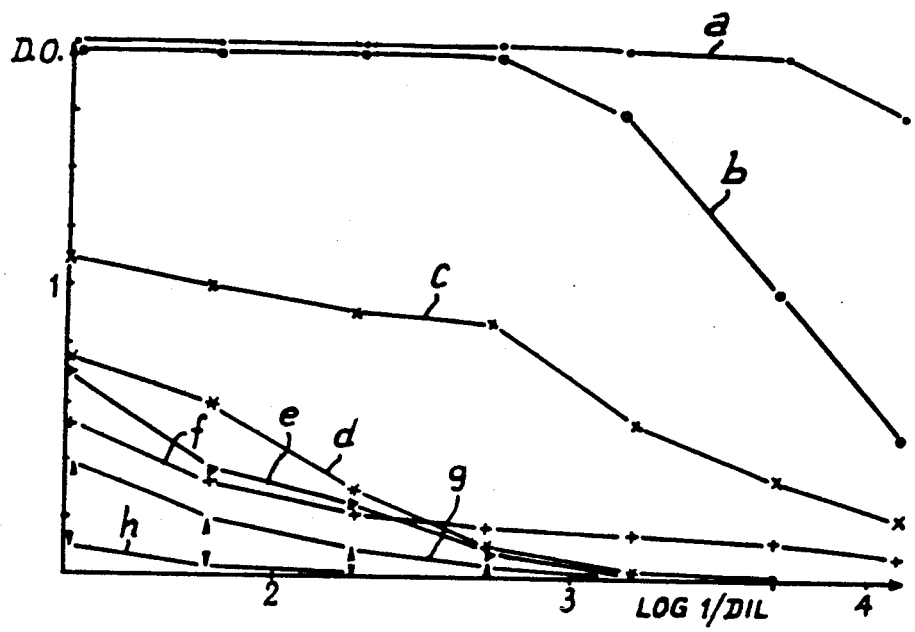
FIG. 7 represents the titration curves of rabbit antipeptide serums against the gp51 glycoprotein.
Figure 8:
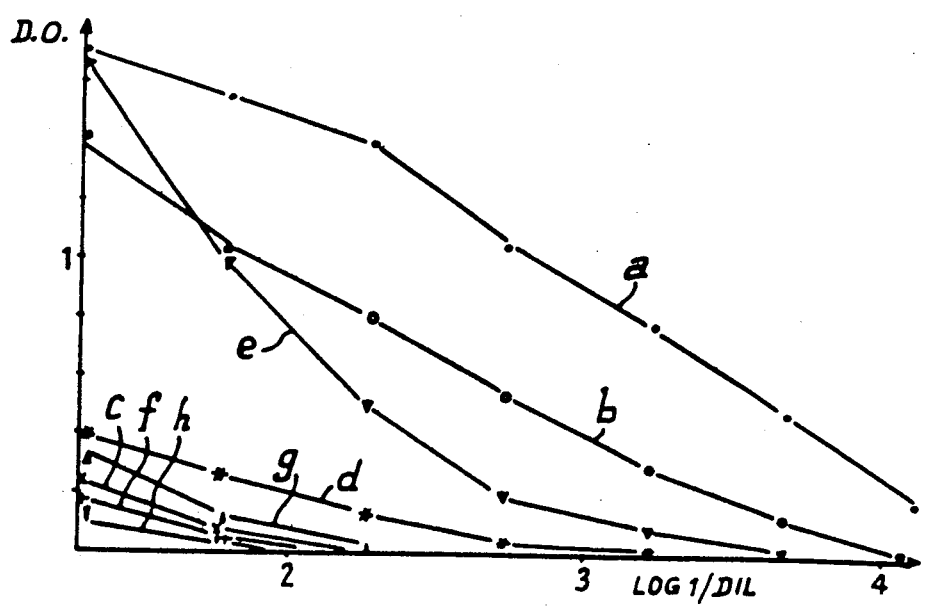
FIG. 8 represents the titration curves of rabbit antipeptide serums against the whole BLV virus.

FIG. 7 shows the titration curves for rabbit antipeptide antiserums against the purified gp51 antigen and on FIG. 8 the titration curves of the antipeptide antiserums against purified BLV viral particles, obtained by the ELISA method applied under the conditions previously indicated. The abscissa shows the log of the inverse of the dilution and the ordinate shows the optical density (O.D) measured at 460 nm.

The curves labelled a are the reference curves obtained with the anti-gp51.

The curves labelled b are the curves obtained with the anti-L255-268.

The curves labelled c are the curves obtained with the anti-B59-69.

The curves labelled d are the curves obtained with the anti-B260-268 and the anti-B144-155.

The curves labelled e are the curves obtained with the linear anti-L78-92 and cyclic anti-L78-92.

The curves labelled f are the curves obtained with the anti-L144-157.

The curves labelled g or h are the curves obtained with the other anti-peptides.

It emerges from these results that when the purified gp51 glycoprotein is used as the antigen, the reactivity in decreasing order is:

anti-gp51 > anti-255-268 > anti-59-69

The other anti-peptide serums present a much weaker activity.

When complete BLV virions are used as the antigen, the order of reactivity is established as follows:

anti-gp51 > anti-255-268 > anti-78-92 (linear or cyclic).

The serums of rabbits which had been immunized with conjugates, were tested to determine their capacity to neutralize the biological activity of the BLV virus. This was evaluated using the test of the inhibition of the VSV (BLV) pseudotypes as described by J. ZAVADA, L. CERNY, Z. ZAVADOVA, J. BOZONOVA and A. D. ALSTEIN in J. Natl. Cancer Inst. 62, p.95–101 (1979).

The pseudotype inhibition test is based on the observations by J. ZAVADA et al, that infection by the vesicular stomatitis virus (VSV) in cells chronically infected with BLV virus provided virus particles in which the genome is that of the VSV and the envelope is that of the BLV virus (pseudotypes).

These VSV/BLV pseudotypes possess the specific properties linked to the envelope glycoprotein gp51 of the BLV virus such as neutralization and host specificity. The VSV genome within these pseudotypes render the particles capable of rapidly (24–36 hours) forming zones of lysis on monkey cells infected with these pseudotypes.

Briefly, for the neutralization of the pseudotypes with the serums to be tested, one mixes 1 ml of a preparation of pseudotypes able to form 200 lysis zones on the cells to be tested ($10^{-1}$, $10^{-2}$, $10^{-3}$, $10^{-4}$ and other intermediate dilutions). These serums have first been inactivated by heating to 56° C. for 30 minutes.

After incubation for one hour at 20°, 0.5 ml of each mixture is inoculated onto a layer of monkey cells in a Petri dish. After 90 mn of incubation, the inoculum is removed by washing with sterile isotonic buffer and the cells are covered with a layer of agar.

After 24–36 hours of incubation at 37° C., the cells are stained with neutral red and the residual lysis zones counted.

The titer in neutralizing antibodies against the BLV virus is obtained by determining the serum dilution at which only 50% of the lysis zones are obtained relative to those occurring in the absence of the serum to be tested. The results are given in Table IV.

It is clear from these results that the antibodies directed against the peptide 78-92 show a remarkable inhibiting capacity on the pseudotypes. In the same way it may be seen that the antibodies against the peptides 39-48 and 144-157 equally show a good capacity to inhibit the pseudotypes.

We have studied the reactivity of a certain number of rabbit serums directed against the gp51 antigen and of the serums of animals infected by the BLV virus, with the chemically synthesized oligopeptides which have then been attached to plastic well surfaces. The results are summarized in Table V, and include only those ovine or bovine serums which gave a response (those not included did not).

The results show that, of the serums tested, a limited number of them recognize the oligopeptides (bovine serums No. 15 and 285, and ovine serums No. 35, 38, 65, 67, 68 and 98). The oligopeptide 78-92 is recognized both by the bovine serum (No. 15) and the ovine serum (No. 65).

In addition, these results permit the following observations to be made:

slight differences have been found in the reactivities of the rabbit serums (serums No. 167 and 2670), which might be explained by the fact that the gp51 preparations administered were not the same and that the receiving animals were different;

the reactivity of a rabbit serum obtained by inoculation of BLV virions is approximately comparable to that of serums from rabbits having had gp51 administered;

the monoclonal antibodies do not react with the oligopeptides coupled to the support.

The oligopeptide 78-92 presents the remarkable property, when linked to a protein carrier, of inducing neutralizing antibodies, giving a particular interest to this oligopeptide, for the development of vaccines.

The immunogenic properties of the oligopeptide 78-92 equally permits its use as a means of diagnosing the presence or not of BLV virus in animal blood samples.

The gp51 glycoprotein fragments or synthetic proteins, according to the invention, may equally be applied as antigens in the search for antibodies, notably for diagnostic or analytic purposes; for the production of antibodies, including monoclonal antibodies, by induction in appropriate hosts; and for the production of vaccines.

TABLE I

| Peptide | Origin of the variant | Amino Acid Sequence | Immunized Rabbit (N°) | Coupling to the protein carrier |
|---|---|---|---|---|
| B 260–268 | T15-2 | SAPPTRVR | 2651 | G/THY |
| L 255–268 | T15-2 | STVSSAPPTRVRR | 2664 | G/KLH |
| B 59–69 | T15-2 | PPPQGRRRFGA | 2638 | G/THY |
| L 57–67 | T15-2 | YWPPPQRRRF | 2662 | G/KLH |
| B 144–155 | T15-2 | PDPPQPDFPQLN | 2698 | G/THY |
| L 144–157 | T15-2 | PDPPQPDFPQLNSD | 2658 | G/KLH |
| L 195–205 | T15-2 | VYNKTISGSGP | 2659 | G/KLH |
| L 21–28 | T15-2 | KFSISIDQ | 2649 | G/KLH |
| L 39–48 | T15-2 | CPRSPRYTDL | 2643 | G/KLH |
| L 39–48 | FLK | CAKSPRYTLD | 2657 | G/KLH |
| L 78–92 | FLK | EPRCPYVGADHFDCP | 2653 | G/KLH |
| L 78–92 cyclic | FLK | EPRCPYVGADHFDCP | 2629 | G/KLH |

TABLE II

| Amino acid | Protective Group |
|---|---|
| Asp | benzylic ester |
| Glu | benzylic ester |
| Ser | benzylic ether |
| Thr | benzylic ether |
| Tyr | O-2,6 dichlorobenzyl |
| His | tosyl |
| Arg | tosyl |
| Lys | chlorobenzyloxycarbonyl |
| Crs | S-acetamidomethyl |

TABLE III

| antiserum obtained against the peptide | Reactivity of the antiserum against: | | |
|---|---|---|---|
| | peptide | purified gp 51 (from FLK cells) | whole BLV (from FLK cells) |
| B 260–268 | +++++ | ++ | ± |
| L 255–268 | +++++ | ++++ | ++++ |
| B 59–69 | +++ | +++ | − |
| L 57–67 | +++ | ± | − |
| B 144–155 | +++ | ++ | ± |
| L 144–157 | +++++ | ++ | + |
| L 195–205 | +++++ | ± | − |
| L 21–28 | +++++ | ± | − |
| L 39–48 | +++++ | − | − |
| L 39–48 | +++++ | ± | ± |
| L 78–92 | +++++ | + | +++ |
| L 78–92 cycl. | +++++ | + | +++ |
| purified anti-gp 51 | / | +++++ | +++++ |

TABLE IV

| antiserum obtained against the peptide | Origin of the virus variant | Inhibition power of the pseudotypes |
|---|---|---|
| B 260–268 | 15-2 | − |

TABLE IV-continued

| antiserum obtained against the peptide | Origin of the virus variant | Inhibition power of the pseudotypes |
|---|---|---|
| L 255-268 | 15-2 | − |
| B 59-69 | 15-2 | − |
| L 57-67 | 15-2 | − |
| B 144-155 | 15-2 | − |
| L 144-157 | 15-2 | ++ |
| L 195-205 | 15-2 | − |
| L 21-28 | 15-2 | − |
| L 39-48 | 15-2 | + |
| L 39-48 | FLK | ++ |
| L 78-92 (linear) | FLK | ++ |
| L 78-92 (cyclic) | FLK | +++ |
| rabbit anti-gp 51 | FLK | +++ |

TABLE V

| peptide | Rabbit 167 purified gp 51 | Rabbit 2670 purified gp 51 | Rabbit 154 BLV virions | Monoclonal antibodies | Bovine serums N° | Ovine serums N° |
|---|---|---|---|---|---|---|
| B 260-268 | ± | − | + | − | − | 68 (+) |
| L 255-268 | ± | +++++ | + | − | 15 (+++) | 35,65,68,98, (+++ +) |
| B 59-69 | +++ | − | ± | − | 285 (+) | 65,67,68 (+) |
| L 57-67 | − | ± | ± | − | − | − |
| B 144-155 | +++++ | ± | +++++ | − | − | 65,67,68 (+) |
| B 144-157 | +++++ | ± | +++++ | − | − | 38,65,68,98 (++++) |
| L 195-205 | − | − | + | − | − | − |
| L 21-28 | ± | − | ± | − | − | − |
| L 39-48 | ± | − | ± | − | − | − |
| L 39-48 | ± | − | ± | − | − | − |
| L 78-92 | +++++ | ++ | ++ | − | 15 (+++) | 65 (+++) |
| L 78-92 cycl. | +++++ | +++ | +++ | − | 15 (+) | 65 (+) |

We claim:

1. A peptide consisting of a sequence selected from the group consisting of the sequences of amino acids corresponding to positions 39-48, 78-92 and 144-157 of the gp51 glycoprotein of bovine leukemia viruses, respectively.

2. A peptide according to claim 1 which is an oligomer of said peptide.

3. A peptide according to claim 1 which is a cyclic peptide obtained by S—S bonding between the two cysteine of the sequence of amino acids corresponding to positions 78-92 of the gp51 glycoprotein.

4. The peptide according to claim 1 consisting of the sequence:

Glu-Pro-Arg-Cys-Pro-Tyr-Val-Gly-Ala-Asp-His-Phe-Asp-Cys-Pro.

5. The peptide according to claim 1 consisting of the sequence:

Pro-Asp-Pro-Pro-Gln-Pro-Asp-Phe-Pro-Gln-Leu-Asn-Ser-Asp.

6. The peptide according to claim 1 consisting of the sequence:

Cys-Pro-Arg-Ser-Pro-Arg-Tyr-Thr-Asp-Leu.

7. The peptide according to claim 1 consisting of the sequence:

Cys-Ala-Lys-Ser-Pro-Arg-Tyr-Thr-Leu-Asp.

8. The peptide according to claim 4 obtained by chemical synthesis.

9. A peptide according to claim 4, 6 or 7 protected on its cysteines.

10. A peptide consisting of two or more of the sequences of amino acids selected from the group consisting of the sequences of amino acids corresponding to positions 39-48, 78-92 and 144-157 of the gp51 glycoprotein of bovine leukemia viruses, respectively.

* * * * *

UNITED STATES PATENT AND TRADEMARK OFFICE
CERTIFICATE OF CORRECTION

PATENT NO. : 5,239,056
DATED : August 24, 1993
INVENTOR(S) : PORTETELLE ET AL

It is certified that error appears in the above-indentified patent and that said Letters Patent is hereby corrected as shown below:

On the title page: Item [75]

after Inventors: change "Daniel G.J.G. Portetellie" to --Daniel G.J.G. Portetelle--.

Signed and Sealed this

Eighteenth Day of July, 1995

Attest:

BRUCE LEHMAN

Attesting Officer  Commissioner of Patents and Trademarks